United States Patent [19]

Aziz et al.

[11] Patent Number: 5,456,908
[45] Date of Patent: Oct. 10, 1995

[54] POLYAMINE-POLYAMINE AND POLYAMINE-PROTEIN TRANSPORT INHIBITOR CONJUGATES AND THEIR USE AS PHARMACEUTICALS AND IN RESEARCH RELATING TO POLYAMINE TRANSPORT

[75] Inventors: Shewan M. Aziz; Mark N. Gillespie, both of Lexington, Ky.

[73] Assignee: The University of Kentucky Research Foundation, Lexington, Ky.

[21] Appl. No.: 203,629

[22] Filed: Mar. 1, 1994

[51] Int. Cl.$^6$ .................. A61K 31/74; A61K 31/785
[52] U.S. Cl. ........................... 424/78.08; 424/486
[58] Field of Search ................... 424/78.08, 486; 514/579

[56]  References Cited

U.S. PATENT DOCUMENTS 4,701,521  10/1987  Ryser ........................ 530/322

FOREIGN PATENT DOCUMENTS 0185218  11/1982  Japan.

Primary Examiner—Gollamudi S. Kishore
Attorney, Agent, or Firm—Burns, Doane, Swecker & Mathis

[57]  ABSTRACT

Novel classes of inhibitors which selectively inhibit the cellular transport of normally transported substances, specifically polyamines are taught which comprise (i) polymers of the transported substance or (ii) protein or polypeptide conjugates of the transported substance. These inhibitors may be used in vitro to assess the effect of the transported substance on cellular functions and in vivo for treating disease conditions involving transport of the particular substance, e.g., a polyamine.

15 Claims, 5 Drawing Sheets

Impact of Put-Put Conjugate on Polyamine Uptake

Impact of Spd-Spd Conjugate on Polyamine Uptake

Impact of Spm-Spm Conjugate on Polyamine Uptake

Impact of Put-BSA Conjugate on Polyamine Uptake

Impact of Spd-BSA Conjugate on Polyamine Uptake

Impact of Spm-BSA Conjugate on Polyamine Uptake

Impact of Put-Put Conjugate on DFMO-stimulated Polyamine Uptake

Impact of Spd-Spd Conjugate on DFMO-Stimulated Polyamine Uptake

Impact of Spm-Spm Conjugate on DFMO-Stimulated Polyamine Uptake

Impact of Put-BSA Conjugate on DFMO-stimulated Polyamine Uptake

Impact of Spd-BSA Conjugate on DFMO-stimulated Polyamine Uptake

Impact of Spm-BSA Conjugate on DFMO-stimulated Polyamine Uptake

POLYAMINE-POLYAMINE AND POLYAMINE-PROTEIN TRANSPORT INHIBITOR CONJUGATES AND THEIR USE AS PHARMACEUTICALS AND IN RESEARCH RELATING TO POLYAMINE TRANSPORT

FIELD OF THE INVENTION

The present invention is directed to polymeric conjugates of substances which are normally actively transported into cells or protein or polypeptide conjugates of such normally transported substances and the use thereof to inhibit uptake of such normally transported substances. The present invention is more particularly directed to polymeric conjugates of polyamines, and conjugates of polyamines and proteins or polypeptides and the use thereof to inhibit the cellular uptake of polyamines.

BACKGROUND OF THE INVENTION

The endogenous polyamines, in particular, putrescine (1,4-butanediamine), spermidine (N-[3-aminopropyl]-1,4-diaminobutane) and spermine (N,N'-bis-[3-aminopropyl]-1,4-butane-diamine) have been the subject of increasing research, due to the growing appreciation of their physiological importance. These polyamines have regulatory roles in tissue growth and interact with nucleic acids, as well as exhibiting a variety of effects upon macromolecular synthesis, expression and metabolism (Tabor et al., *Ann. Rev. Biochem.*, 30, 597 (1961); Janne et al., *Biochem. Biophys. Acta*, 473,241, (1978); and Tabor et al., *Ann. Rev. Biochem.*, 45,285 (1976)).

Accounts on the biochemistry, regulation and potential functions of polyamines may be found in recent review articles (Tabor et al., *Ann. Rev. Biochem.*, 53,749 (1984); Pegg et al., *Ann. J. Physiol.*, 243, C212 (1982); Pegg, *Biochem J.*, 234, 249 (1986); Seiler et al., *Acta Biochem. Biophys. Hung*, 23, 1 (1988); and, Seiler et al, *Int. J. Biochem.*, 22, 211, (1990)) from which most of this background discussion is excerpted.

Polyamine homeostasis and adjustment of the intracellular concentrations to physiological requirements are regulated by both synthetic and catabolic reactions. De novo biosynthesis can in principle be substituted by polyamine transport from the environment.

In cells lacking amine oxidases which oxidatively deaminate polyamines, the release of intracellular polyamines is essential for the regulation of polyamine cellular concentrations. Currently available evidence suggests that $N^1$-$N^2$-diacetylspermine may also fulfill regulatory requirements. The actual signals which control polyamine release are not known. However, there exists strong evidence in the scientific literature that the proportion of N'-acetylspermine and N'-acetylspermidine which remains intracellular and which is oxidatively cleaved into spermidine and putrescine is controlled by outward transport (Seiler, *J. Physiol. Pharmacol.*, 65, 2034 (1987)).

In vivo studies involving the metabolism of labeled polyamines have shown that polyamines may be taken up by tissues from the circulation. It is further well known that some tissues exhibit a high demand for polyamines. Examples of such tissues include the prostate (Clark et al., *J. Nucl. Med.*, 16, 337 (1975)), tumor cells (Volkow et al., *Science*, 221,673 (1983)) and normal but rapidly proliferating cells (Jänne et al., *Acta Chem. Scand.*, 20, 1174 (1966); Seiler et al., *Brain Res.*, 22, 81 (1970)). Enhanced uptake of $^{14}$C-labeled polyamines by tissues with depleted polyamine stores has repeatedly been observed (Chaney et al., *Life Sci.*, 32, 1237 (1983); Huston et al., *Cancer Res.*, 44, 1034 (1984)).

Recently, much research has been undertaken to characterize and understand the particular transporters which control polyamine uptake in mammalian cells. Early work on polyamine transport related to bacteria and other microbia and is reviewed in Tabor et al., *Pharmac. Rev.*, 16, 245 (1964) and Bachrach, "Function of Naturally Occurring Polyamines," pp. 51–52, Academic Press, N.Y. (1973). Other papers describing polyamine transport in specific microbia are also available in the literature (Davis et al., *Arch. Biochem. Biophy.*, 267,479 (1988) and Kashiwagi et al., *J. Bact.*, 165, 972 (1986)).

Polyamine uptake systems in mammalian cells resemble the uptake systems of amino acids. Accordingly, most researchers studying polyamine transport have used research strategies which have had prior success in characterizing amino acid uptake.

To date there still exists no complete understanding of polyamine transport systems in mammalian cell lines. However, from what is disclosed in the literature, it appears that polyamine transport is energy and temperature dependent, and saturable. Therefore, it seems that it is a carrier-mediated transport system. An exception is polyamine transport into perfused rabbit lung or lung slices which appears not to be energy dependent or $Na^+$ activated, suggesting that polyamine uptake into the lungs of this species may instead occur via diffusion (Rao et al., *Biochem. Biophys. Acta*, 966, 22 (1988)) rather than an active carrier system. Polyamine uptake in lungs of other species, including rats, is saturable and energy-dependent (Rannels et al).

Available evidence suggests that macromolecular synthesis of RNA and promins is required to adapt polyamine transport to enhanced polyamine requirement (Martin et al., *Int'l. Symp. Polyamines in Biochem. Clin. Res.*, Sorrento (Italy), Abst. p. 67 (1988). Most cells appear to have a single transporter for putrescine, spermidine and spermine as shown by competitive studies. However, some cells appear to have more than one pathway for polyamine uptake wherein each transporter comprises a different affinity for putrescine, spermidine and spermine (Kumagai et al., *Am. J. Phys.*, 254, G81 (1988); Minchin et al., *Int'l. Symp. Polyamines Biochem. Clin. Res,*, Sorrento (Italy), Abst. p. 67 (1988); Byers et al., *Am. J. Physiol.*, 252, C663 (1987); Feige et al., *Biochem. Biophys. Acta*, 846, 93 (1985); and De Smedt et al., *Biochem. Biophys. Acta*, 1012, 171 (1989)).

The affinity for the carrier increases from putrescine to spermidine and spermine with published $K_m$ values in the low µM range. Polyamine transport is observed in the absence of sodium; however, the increase of sodium to physiological concentrations (116 mM) usually increases the transport rate by 60%. Dissipation of the sodium gradient by ionophores has been shown to inhibit the sodium-dependent portion of polyamine uptake.

While high affinity sodium-activated transport is usually observed, some cell types exhibit sodium-independent polyamine uptake. For example, in LLC-PK1 renal epithelial cells both the sodium-activated and the sodium-independent transport systems were saturable. By contrast, in adrenocortical cells the sodium independent transport system was not saturable and preferentially transported spermine (Feige et al., *Biochem. Biophys. Acta*, 846, 93 (1985)).

Activation of polyamine transport into mammalian cells by thiols (glutathione, dithiothreitol) and inhibition by thiol reagents (p-chloromercuribenzene sulfonate, N-ethylmaleimide) has been studied by many researchers. The results obtained by these researchers suggest that the sodium-activated transporter requires thiol groups to maintain active conformation.

The amino acid uptake pathways are generally regarded as different from polyamine transporters systems. However, a number of amino acids (asparagine, glutamine, serine, alanine and α-(methylamino)isobutyric acid) stimulate at 0.5 mM concentration putrescine uptake into a neuroblastoma cell line (Rinehart et al., *J. Biol. Chem.*, 259, 4750 (1984)) and that some basic amino acids exhibit a very weak inhibitory effect on polyamine uptake.

The polyamine transporter does not appear to be specific for putrescine, spermidine or spermine. Therefore, it is likely that polyamine analogs are transported by the same system. Some researchers have compared a series of homologous diamines and triamines in relation to their ability to inhibit competitively the uptake of labelled putrescine, spermidine and spermine by L1210 leukemia cells. 1,7-Heptene diamine followed by 1,8-octanediamine and 1,6-hexanediamine were most potent among the diamines, while triamines were generally more effective as uptake competitors. Maximum inhibition was achieved using amines having comparable chain lengths to spermine and spermidine. This is consistent with the understanding in the art that the recognition site of the polyamine transporter contains at least three negatively charged groups in a distance corresponding to the distance between the positively charged nitrogen atoms of spermidine, presumably in its most stable all-trans configuration. (Gordon-Smith et al., *Biochem. Pharmacol.*, 32, 3701, (1983)).

The primary amine groups of the polyamines seem to be essential for uptake. For example, N-alkyl substituents on the terminal amino groups of putrescine, spermidine or spermine decrease the ability of these compounds to competitively inhibit uptake. Also, substituents (F, Cl, OH, $CH_3$) in the last two positions of the carbon chain of putrescine reduce polyamine uptake.

Methylglyoxal-bis(guanylhydrazone) (MGBG), an antileukemic drug which inhibits S-adenosylmethionine decarboxylase and which exhibits a structure highly similar to spermidine shares the polyamine transport system. The potent cytotoxicity of this compound thereby afforded researchers a selection method for identifying Chinese hamster ovary cells incapable of MGBG and polyamine transport (Mandel et al., *J. Cell. Physiol.*, 97, 335 (1978). Genetic studies indicate that more than one gene locus is involved in MGBG uptake by these cells (Heaton et al., *J. Cell. Physiol.*, 136, 133 (1988)).

Also, it is believed that such polyamine transport mutants should play a major role in identifying genes involved in polyamine transport, for studying the regulation of transport, and for studying the role of polyamine transport in proliferating cells and in some related disease conditions such as cancer.

For example, Ask et al. recently studied increased survival of L1210 leukemic mice by preventing utilization of extracellular polyamines using an L1210 leukemic cell line (L1210-MGBG') deficient in polyamine transport. Their results indicated that leukemic mice bearing the polyamine uptake mutant cells exhibited a cure rate of 33% when polyamine synthesis was blocked by DFMO. By contrast, mice having non-mutant polyamine transport L1210 cells only had a two day increase in survival time after similar DFMO treatment (Ask et al., *Cancer Lett.*, 66, 29 (1992)).

The polyamine uptake system has been implicated in the uptake of other drugs as well. For example, paraquat (N,N'-dimethyl-4,4'-dipyridylium) has been shown to inhibit the uptake of MGBG, putrescine and spermidine, but with no apparent effect on spermine uptake (Smith et al., *Biochem. Pharmac.*, 30, 1053 (1981)).

Also, some researchers have attempted to design cytotoxic drug conjugates which are similar in structure to endogenous polyamines so that they are transported by the polyamine transport system. For example, Holley et al. recently synthesized a series of 2- and 5-nitroimidazole-polyamine conjugates which were apparently transported by the polyamine transport system. Of the compounds tested, the 2-nitroimidazole-polyamine conjugates were the most potent inhibitors of spermidine uptake (Holley et al, *Biochem. Pharmacol.* 43,763, (1992)).

Also, several bipyridinium, tetrapyridinium and hexapyridinium quaternary salts have been found to be potent inhibitors of putrescine uptake into B16 melanoma cells which have previously treated with difluoromethylornithine, with the potency of inhibition being apparently directly related to the number of quaternary centers (Minchin et al., *Biochem. J.*, 262, 391 (1989).

Some inhibitors of polyamine uptake have been discovered which are structurally unrelated to polyamines. For example, the cationic peptide melittin and another calmodulin antagonist, 1.3-dihydroxy-1-(4-methyl)- 4H,6H-pyrrolo [1,2-9][4,1]-benzoxazepin-4-yl)methyl]-4-piperidinyl]-2H-benzimidazol- 2-one (CG 59373B) inhibits putrescine uptake into human prostate cells. Trifluoropiperazine, a calmodulin antagonist and protein kinase C inhibitor also inhibits polyamine uptake as does the protein kinase C inhibitor H7 (1-(5-isoquinolinylsulfonyl)-2-methyl-piperazine). Also, treatment of leukemia cells with phorbyl esters activates proteinase kinase C and has been shown to enhance spermidine uptake into murine leukemic cells. It therefore appears that protein kinase C may play a role in polyamine transport.

Various factors are believed to affect the uptake of polyamines into mammalian cells including (i) availability of polyamines in vivo, (ii) intracellular polyamines, (iii) the sialic acid coating on the cell membrane, and (iv) the growth state of the particular cells.

The availability of polyamines in the circulation is believed to be important in polyamine transport. Putrescine and spermine blood concentrations are low in comparison to spermidine (Claverie et al., *Anticancer Res.*, 7, 765, (1987)). This is surprising given that the electrostatic binding of spermine to negatively charged groups is higher than for spermidine and putrescine. Accordingly, one would expect the concentration of free spermine to be extremely low, particularly in light of the fact that red blood cells have a negative surface charge and efficiently bind polyamines. Further evidence of the importance of spermidine uptake is the fact that the $V_{max}$ of spermidine is higher than that of spermine, despite its lower affinity to the transporter.

The level of intracellular polyamines is also believed to affect polyamine uptake. Depletion of intracellular polyamines has been found to generally enhance polyamine uptake several-fold. As in the case of circulating polyamines, the concentration of free intracellular polyamines is probably involved in regulation of uptake.

As noted above, the sialic acid coating on cell membranes is believed to have some effects on polyamine transport. The removal of N-acetylsialic acid from the surface of murine leukemia cells by incubation with neuraminidase enhances spermidine uptake. Re-sialated cells regain normal transport rates (Khan et al., *Biochem. Arch.*, 5, 161 (1989)). It is believed by some researchers that the sialic cell surface coating nonspecifically binds positively charged polyamines via the carboxyl group of the sialic acid residues thereby diminishing effective concentration of transport substances at the transporter site.

Polyamine transport is also believed to be important for the ability of cells to adapt to changes in polyamine requirements. Enhanced cell growth rates are usually accompanied by both enhanced intracellular de novo synthesis and enhanced uptake of polyamines.

Trophic stimuli, including hormones and growth factors, have been observed to enhance polyamine transport rates (Pohjanpelto, *J. Cell. Biol.*, 68, 512 (1976), DiPasquale et al., *Exp. Cell. Res.*, 116, 317 (1978)). In these studies stimulation of human fibroblasts to cell proliferation by serum or epidermal growth factor was followed by an 18–100 fold increase of ornithine decarboxylase activity.

Also, stimulation of mouse mammary glands with insulin caused the increase of $V_{max}$ for spermidine and prevented effects thereof (Kano et al., *J. Biol. Chem.*, 251, 2795 (1976)). However, it is unknown whether the hormone induced formation of the carrier or decreased carrier inactivation.

Some studies have shown that transformed cells transport polyamines better than their normal counterparts. However, in at least one study involving EJ2-ras transfected cells polyamine turnover was enhanced but transport rates remained unaffected. In contrast, N-myc transfection enhanced polyamine uptake with no affect on biosynthesis (Chang et al., *Biochem. Biophys. Res. Comm*, 157, 164 (1988). Thus, there exists circumstantial evidence that polyamine uptake and synthesis may be regulated by different genes. Perhaps not unexpectedly, cells exhibiting reduced growth rates have been observed to decrease polyamine uptake. For example, cells approaching cell confluency because of high cell density decrease polyamine uptake. Also, when cells are induced to differentiate and therefore reduce their rate of proliferation, their demand for polyamine has been found to diminish.

As discussed above, cellular concentrations of polyamines are regulated by at least two important pathways. The first, and best understood, involves de novo biosynthesis. The rate of cellular polyamine synthesis is governed by the activity of the enzyme ornithine decarboxylase (ODC) which catalyzes the conversion of the amino acid ornithine to the diamine putrescine. Putrescine, in turn, is then convened sequentially to spermidine and spermine by two other enzymes. The role of ODC in regulation of cell polyamine contents and its potential suitability as a pharmacological target has been facilitated by the development of DFMO, (α-difluoro-methylornithine), a highly selective and potent inhibitor of this enzyme. In some instances, inhibition of ODC with DFMO is highly effective in depleting cell polyamine cell contents and arresting cell proliferation. However, in other instances the cells seem to use compensatory pathways to maintain adequate polyamine concentrations. Results of human clinical trials with DFMO have, in general, been disappointing. Though the drug is beneficial in treating some non-neoplastic diseases (e.g., infectious conditions), its therapeutic efficacy in cancer appears to be limited.

The reason for the poor results with DFMO is believed to be attributable to the polyamine transport system of cells. As discussed supra, along with de novo polyamine synthesis, cells are apparently capable of regulating and accumulating polyamines across their plasma membrane via an energy-dependent transport system. Work by the present inventors and others suggests that most cells express at least two pathways for polyamine uptake. The first comprises a non-selective pathway for putrescine, spermidine and spermine and the second comprises a pathway which is selective for spermine and spermidine. Both pathways are markedly increased when ODC activity is depressed, either by pathologic changes or by treatment with DFMO, and are thereby able to compensate for decreased de novo polyamine synthesis. Because there exist no pharmacological agents which selectively inhibit polyamine transport, the suitability of this pathway as a pharmacological target has as yet not been adequately established.

As discussed above, most previous attempts to design inhibitors of polyamine transport have focused on polyamine analogues with a few exceptions involving several calmodulin antagonists and protein kinase C inhibitors. However, the previously examined molecules have either lacked specificity and/or exhibited unacceptable toxicity. Thus, there still exists a substantial need in the art for effective polyamine transport inhibitors which selectively inhibit the transport of specific polyamines while not exhibiting unacceptable toxicity and while not affecting the transport of other transported substances. Also, there exists a need in the art for a convenient and reproductive method for obtaining transport inhibitors of desired substances.

OBJECTS OF THE INVENTION

It is an object of the invention to obviate the problems observed with previous transport substance inhibitors, e.g., non-specificity and toxicity.

It is another object of the invention to provide novel inhibitors of transport of substances normally actively transported by cells which selectively inhibit the uptake of the targeted substance into such cells, which comprise polymeric conjugates of the transported substance or a protein or polypeptide conjugated to the transported substance.

It is a further object of the invention to use such novel transport inhibitors of targeted substances which comprise polymers of transported substances or polypeptide or protein-transported substance conjugates in vitro to study the role of the uptake of the targeted substance which is normally actively transported on various cellular processes and cell functions.

It is another object of the invention to administer such novel transport inhibitors of normally transported substances which comprise polymeric conjugates of transported substances or protein or polypeptide-transported substance conjugates in vivo to treat disease conditions which involve transport of the particular transported substance.

It is a specific object of the invention to provide novel polyamine transport inhibitors which comprise polymers of polyamines or polyamine-protein or protein conjugates which selectively inhibit uptake of a targeted polyamine and which do not exhibit undesirable toxicity.

It is another specific object of the invention to use novel polyamine transport inhibitors which comprise polyamine polymers or polyamine-protein or polypeptide conjugates which selectively inhibit cellular uptake of targeted polyamines in vitro to study the effect of the particular targeted polyamine on cellular functions.

It is yet another object of the invention to administer novel polyamine transport inhibitors which comprise polyamine polymers or polyamine-protein or polypeptide conjugates selectively inhibit the transport of targeted polyamines for treating disorders wherein polyamine transport is involved in the disease condition, e.g., cancer.

It is yet another object of the invention to provide novel pharmaceutical compositions for treating disease conditions relating to the transport of a targeted substance which contain an effective amount of a novel inhibitor comprising a polymer of the transported substance or a transported substance-protein or polypeptide conjugate which selectively inhibits the cellular uptake of the targeted substance.

It is still another object of the invention to provide novel pharmaceutical compositions for treating diseases wherein polyamine uptake is involved in the disease condition comprising administering an effective amount of the subject novel polyamine transport inhibitors which comprise polymers of polyamines or polyamine-protein or polypeptide conjugates.

BRIEF DESCRIPTION OF THE INVENTION

Previous attempts to design substances which inhibit the cellular uptake of normally transported substances have in general focused on synthesizing analogues of the normally transported substance. A case in point are the previously synthesized polyamine transport inhibitors which were in general substances having structural similarity to transported polyamines.

The rationale behind such an approach is that if the particular analogue is similar enough in structure to the normally transported substances it will be transported into the cell by the same cell transport system. Therefore, it should provide for the competitive inhibition of uptake of the targeted substance.

While this approach works in some instances, it is fraught with many inherent problems. For one, it is sometimes difficult to synthesize an analogue of the targeted transported substance which is capable of being effectively transported into the cell by the same transport system and which competitively inhibits the transport of the targeted substance. Another problem is that the particular analogue, even if transported, may exhibit undesirable toxicity which prevents its in vivo usage. Examples of such compounds include antineoplastic agents such as methylglyoxalbis(guanylhydrazone) (MGBG) which while mimicking the structure of endogenous polyamines and inhibiting the transport thereof possess a high degree of toxicity.

Yet another problem with the design of effective inhibitors involves designing substances which specifically inhibit the uptake of a targeted substance while not inhibiting the uptake of other non-targeted substances. This is essential for in vitro studies if one is to be able to elucidate the cellular functions affected by the particular targeted substance. Also, it is important for in vivo usage in the use of such inhibitors for treating disease conditions wherein one desires to inhibit uptake of an undesirable targeted substance while not preventing uptake of other substances which may be essential for well being.

The present inventors have discovered two novel classes of transport inhibiting substances which differ fundamentally from previous transport inhibitors. These inhibitory substances comprise a modification of a well-accepted approach for constructing conjugates between endogenous chemicals that are normally actively transported into cells and low-molecular weight drugs as a means for enhancing the uptake of the drug. However, the subject transport inhibitors obtain a substantially different function and result in that they are not themselves transported into cells but instead selectively inhibit the transport system of the cell which is responsible for uptake of the targeted transported substance, e.g., a polyamine.

The first class of transport inhibitory substances discovered by the present inventors comprises polymeric conjugates of the targeted transported substance wherein the repeating units of the polymer comprise the particular targeted transported substance. These moieties may be directly linked or may be indirectly attached using known coupling agents. It has been surprisingly discovered that polymers of a targeted normally transported substance, e.g., a polyamine such as putrescine, spermine or spermidine, may be used to selectively block transport of the transported substance. By selective it is meant that these polymers do not block transport of non-targeted substances such as amino acids and other normally transported substances. Also, these polymers appear to act at the level of the cell membrane and do not appear to enter the cells. This is in contradistinction to previous transport inhibitor analogues and transported substance-drug conjugates wherein the analogue or the drug was apparently internalized by cells.

The second novel class of transport inhibitory substances discovered by the present inventors to effectively and selectively inhibit transport of a targeted substance comprises conjugates of the targeted transported substance and a protein or polypeptide, preferably a protein or polypeptide that does not exhibit undesirable toxicity. It has been surprisingly discovered that when a normally transported substance is conjugated to a protein, that the resulting conjugates are capable of selectively inhibiting the uptake of the specific targeted substance. Also, as with the aforedescribed polymeric conjugates, these transported substance-protein conjugates apparently operate at the cell membrane and are not actively transported into cells. The targeted transported substance may be directly coupled to the particular protein, or may be attached by use of available coupling agents. In the preferred embodiment the targeted transported substances will comprise endogenous transported polyamines, e.g., putrescine, spermine and spermidine.

Given the ability of these two classes of transport inhibiting substances to selectively inhibit transport of targeted substances they comprise utility in vitro for studying the cellular functions affected by a specific targeted transported substance such as, e.g., a polyamine. Also, they comprise in vivo utility as therapeutic agents for selectively blocking transport of a targeted substance involved in a particular disease condition.

In the preferred embodiment the targeted transported substances will comprise polyamines such as putrescine, spermine and spermidine which are believed to be involved in disorders involving unrestrained cell proliferation and/or differentiation such as cancer, vascular diseases such as hypoxic pulmonary hypertension and other hypertensive pulmonary vascular diseases, systemic hypertensive diseases, intimal hyperplasia secondary to balloon angioplasty ("re-stenosis"), intimal hyperplasia which may result in prosthetic vascular graft failure, cerebral ischemic injury, hyperproliferative skin diseases such as psoriasis leukemia, gastric ulcer, hyperpoxic lung injury, and infectious diseases such as those caused by parasitic protozoa.

However, the invention has broad utility in treating any disease condition wherein the onset or progression of the disease condition requires the uptake of a specific substance

DETAILED DESCRIPTION OF THE INVENTION

Figure 1A:
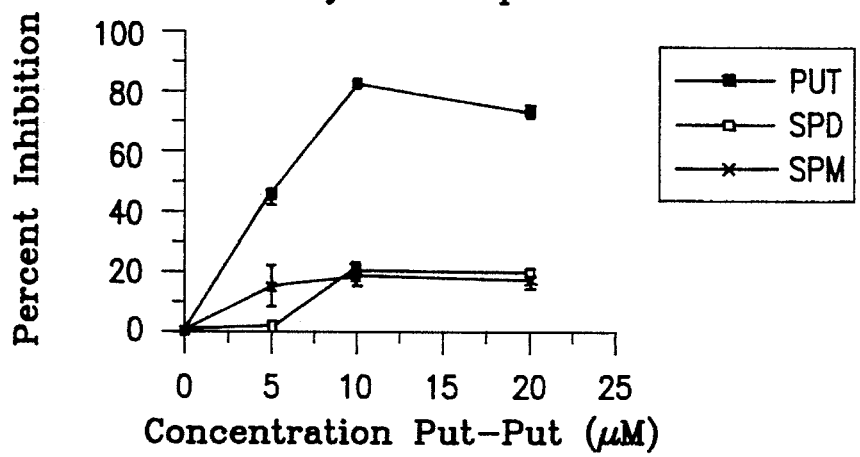
FIGS. 1A–1C: Effect of polyamine-polyamine conjugates, putrescine-putrescine (top), spermidine-spermidine (middle), and spermine-spermine (bottom) on uptake of free $^{14}$C-polyamines in cultured pulmonary artery smooth muscle cells. Conjugates were added to the cultures simultaneously with 3 µM of a specific $^{14}$C-polyamine and allowed to incubate for 30 minutes after which the content of cell-associated radioactivity was determined. Each point is the mean ± the standard error of at least 6 replicates. These data indicate that the Put-Put and Spm-Spm conjugates discriminate between the non-selective and selective spermidine/spermine transport systems and that the Spm-Spm conjugate effectively blocks the import of all three polyamines.

The transport inhibitory substances of the present invention may be synthesized by known methods and reagents for conjugating desired substances. As discussed supra, the conjugates between the targeted substance and the protein or polymers of the targeted substance may be directly linked or may be linked using known coupling agents. The selection of the specific coupling agent or reagent is largely a matter of convenience and depends upon factors including the available coupling agents and the specific targeted substance being conjugated and functional groups which are available for covalent attachment. Examples of suitable coupling agents include, homo and heterobifunctional coupling agents and reagents such as cyanogen bromide, diisocyanates, dialdehydes, glutaraldehydes, carbodiimides, in particular, N-(8-maleimidobutyryloxy)-succinimide, 6-maleinimido-hexanoic acid N-succinimidyl ester (MHS), N-succinimidyl 3-(2-pyridyl dithio)propionate (SPDP), and 1-ethyl-3-(3dimethylaminopropyl)carbodiimide.

Methods for conjugating proteins and other organic substances and reagents for facilitating such attachment are well known in the art and are not a subject of the present invention.

The polymeric transport inhibiting conjugates of the present invention will comprise a sufficient number of molecules of the particular transported substance such that the conjugate is of a sufficient molecular weight to inhibit uptake of the targeted substance without itself being internalized by cells which normally uptake the targeted substance.

The molecular weight of the subject polymeric conjugates of transported substances may vary from about 3,000 to about 500,000, more preferably from 15,000 to about 100,000 and most preferably from about 15,000 to about 30,000. For example, efficacious polymeric polyamine conjugates (which blocked transport of the particular polyamine monomer and which were apparently not themselves internalized) were synthesized using putrescine, spermine or spermidine as the polyamine monomer and glutaraldehyde as the coupling agent which comprised molecular weights in excess of 15,000.

In general, the subject polymeric conjugates will comprise the generic homopolymeric structure:

$$(TS)_n$$

wherein TS is a normally transported substance, and n comprises the number of such moieties. However, as discussed supra, the TS moieties, e.g., a polyamine, may also be indirectly attached using a coupling agent such as glutaraldehyde.

The invention further embraces heteropolymeric conjugates wherein the repeating monomeric units in the polymer comprise several different transported substances, e.g., heteropolymers wherein the monomeric units comprise different polyamines. Thereby, the resulting polymeric conjugate should provide for the selective inhibition of cellular uptake of each of the different polyamines contained in the polymeric conjugate.

The subject polymers of transported substances, e.g., polyamines, may further be conjugated to a moiety which provides for the targeting of the conjugates to desired cells. For example, the subject transported substance polymers may be attached to cell surface antigens, receptors, glycoproteins, and lectins which are expressed on cells involved in a particular disease condition such as cancer.

The second novel class of novel inhibitors discovered by the inventors comprises conjugates of a transported substance and a protein. These conjugates will in general comprise the generic formula:

(TS)—(P)

wherein TS is a normally cellularly transported substance, e.g., involved in a particular disease condition and P comprises a protein or polypeptide, e.g., a biologically acceptable protein or polypeptide. The transported substance and the protein or polypeptide may be directly conjugated or may be indirectly attached using coupling agents such as were described supra. Methods for conjugating proteins or polypeptides to desired compounds are well known to those of skill in the art. The particular coupling method, reagents, and coupling agent are again largely a matter of convenience. Also, the preferred coupling agent again comprises glutaraldehyde.

The protein or polypeptide to which the transported substance is attached will comprise any protein of sufficient molecular weight to provide a conjugate which selectively blocks cellular uptake of the particular transported substance and which itself is not internalized. Also, the selected polypeptide should preferably not be toxic. In the preferred embodiments such proteins will comprise proteins of known application in protein conjugates for in vivo usage such as globulins and albumin proteins, e.g., bovine serum albumin, ovalbumin, key hole impact hemocyanin and human serum albumin.

As stated supra, the molecular weight of the subject transported substance-drug conjugates should be sufficient to block transport of the particular transported substance and be such that the conjugate is substantially non-internalized. The molecular weight of such conjugates will typically range from about 10,000 to about 500,000, preferably from about 50,000 to about 250,000 and most preferably from about 65,000 to 100,000.

In the preferred embodiment the transported substance will comprise a polyamine, e.g. , putrescine, spermine or spermidine. It is also within the scope of the present invention to attach the protein or polypeptide to several different transported substances, e.g., polyamines, to provide a conjugate which inhibits the cellular uptake of several normally transported substances.

As with the polymeric or transported substance conjugates, the subject transported substance-protein or polypeptide conjugates may optionally be attached to a moiety which provides for these conjugates to be selectively targeted to desired cells, e.g., cancer cells, or the polypeptide or protein used for conjugation may itself provide for targeting to specific cells.

Examples of suitable targeting moieties include cell surface antigens, receptor proteins and polypeptides, single chain antibodies, glycoproteins, lectins, etc., which selectively bind to moieties expressed on specific cells wherein the uptake of a normally transported substance is to be inhibited. For example, a polyamine such as spermidine, spermine or putrescine may be conjugated to a specific cancer cell surface polypeptide or protein to provide conjugates which are selectively targeted to cancer cells and which inhibit the uptake of the respective polyamine by such cells.

The selection of a particular targeting moiety will of course depend upon the targeted cells. For example, if such targeted cells comprise cancer cells, the targeting moiety will preferably comprise a ligand which binds to a moiety expressed on the surface of such cancer cells.

As discussed supra, in the preferred embodiment the transported substance contained in the subject transported substance polymeric complexes or transported substance-protein or polypeptide conjugates will comprise one or more polyamines or acetylatal derivatives thereof, and most preferably spermine, spermidine or putrescine.

However, the invention has broad applicability in providing conjugates which selectively inhibit the cellular uptake of any normally transported substance. Examples of transporter pathways other than that for the polyamines contemplated for use in the invention include amino acids, multiple drug resistance transporters such as p-glycoprotein (p-gp), lipoproteins such low density lipoprotein (LDL), neurotransmitters, scrotonia, sugars, homones, succharides, lipids, organic anions and cations, purines and steroids.

The subject transported substance polymeric conjugates and transported substance-protein or polypeptide conjugates have useful in vivo and in vitro applications for selectively blocking cellular transport of the particular transported substance or substances.

In vitro usage will include the addition of the subject conjugates to cell cultures which comprise a cell which normally uptakes the particular transported substance, thereby the effect of uptake of the particular substance on cellular functions may be delineated. In the case of polyamines this will be highly beneficial since millions are spent in laboratories around the world to conduct studies relating to the cell biology of polyamines. However, prior to the present invention there were no pharmacological agents which selectively inhibited the polyamine transport system.

Particular examples of cells wherein polyamine transport is believed to be important include actively proliferating cells such as cancer cells and vascular cells, such as pulmonary vascular cells. For example, it is believed that pulmonary hypertension caused by hypoxia occurs by a biological mechanism involving increased polyamine transport rather than increased de novo polyamine synthesis. Thus, the subject conjugates should facilitate further study of the mechanism of pulmonary hypertension and hypoxia.

In the case of cancer, it is believed that polyamine transport is required for the proliferation of such cells. Also, it is known that many cancer cells express a specialized membrane pump called the "Multiple Drug Resistance" (MDR) transporter. This is an important system for it enables cancer cells to develop resistance to anti-tumor agents by effectively pumping the anti-tumor agent out of the cells. One MDR transporter has been characterized by previous researchers to comprise a 12 domain protein which spans the cell membrane. Among the numerous 12-domain membrane spanning proteins known, one is a putrescine transporter found in bacteria. This, coupled with the fact that both of these transport systems are actively expressed in cancer cells lead the present inventors to believe that these systems may be related. However, the present inventors do not wish to be bound by any theory.

Data contained infra supports the inventors' belief and further indicates that polyamine transport results in potentiation of the activity of anti-rumor agents. Therefore, the subject polyamine inhibitors possess utility in that they provide further in vitro evidence as to relatedness of these two transport systems. Also, they possess utility in that they assist in identifying in vitro anti-rumor compounds whose activity may be potentiated by the addition of polyamine transport inhibitors.

The amount of the subject inhibitor conjugates which are added to a particular cell culture will comprise an amount which is at least sufficient to inhibit transport of the particular transported substance, e.g., a polyamine. In general, the amount of the particular inhibitor conjugate added to the cell culture will range from about 0.001 µM to about 500 µM, preferably from about 0.1 to about 100 µM, and most preferably from about 0.1 µM to about 20 µM. However, this amount will vary dependent upon the nature of the particular conjugate, the substance for which cell uptake is being inhibited, the particular cells being cultured and their capability to transport this substance.

In the case of polyamine transport inhibitors, effective dosages can readily be determined by adding incremental amounts of the particular conjugate to cell cultures and assessing the effect on polyamine uptake using well known assays described, e.g., in Kameji et al, *Amer. J. Physiol.*, 256 (Cell Physiol 25), C160–C167, 1989; Morgan et al, *Biochem J.*, 256, 413–417, 1992; Rannels et al, *Am. J. Physiol*, 287, L346–L353 1989; Kamagai et al, *Amer. J. Physiol*, 256, G905–G910, 1989; Nicolet et al, *Biochem. J.*, 269, 629–632, 1990.

The subject transport inhibitor conjugates also comprise in vivo use both from a research and therapeutic standpoint. For example, the subject conjugates may be administered to animals, e.g., mice, rats, monkeys, and the like to study the effect of inhibited transport of the particular substance on a particular disease condition. In particular, the subject polyamine transport inhibitors may be administered to animals having a condition involving polyamine transport, e.g., cancer, vascular disorders such as pulmonary hypertension and other hypertensive pulmonary vascular disorders, infectious disorders, hyperproliferative skin diseases, cerebral ischemic disorders, etc. Thereby, the in vivo role of polyamine transport on the particular disease condition may accurately be assessed.

An important application of the subject conjugates will involve administration of the subject conjugates to animals having implanted tumors or cancer cells, e.g., rats, as studying the effect of the conjugates on tumor growth and metastasis. Also, the subject conjugates may be administered in conjunction with one or more anti-tumor agents to animals having implanted tumors. Thereby, the effect on efficacy of the particular anti-tumor agent by the particular conjugate may be assessed. As discussed supra, given the similarities of the MDR pump and the polyamine transport system, and the data obtained by the present inventors, it is expected that the subject polyamine conjugates will potentiate the efficacy of many anti-tumor agents by reducing the efficiency of the MDR pump. Also, such in vivo studies will provide further evidence regarding the biological link between these two transport systems.

The amount of the particular conjugate which is administered to an animal will depend upon factors such as the particular animal, the specific disease condition, the particular nature of the conjugate, and the specific transported substance for which uptake is to be inhibited. In general, the amount administered will provide for levels of polyamines in the blood ranging from about 0.001 to 5000 µM, preferably about 0.01 to 2000 µM in the blood, and most preferably will provide for polyamines blood levels ranging from about 0.1 µM to 200 µM.

Another important in vivo usage of the subject polyamine transport inhibitor conjugates will comprise administration to animals, e.g., rats, to evaluate the effect of these conjugates on the induction of fibronectin synthesis and other cellular events by hypoxia in pulmonary artery smooth muscle cells and the effect on pulmonary arterial blood pressure. Such animal studies will provide in vivo evidence that increased polyamine transport is involved in hypoxic pulmonary hypertension. Also, it should facilitate the design of suitable pharmacological agents for treating this condition.

The subject transport inhibitor conjugates will be administered to animals by known methods for administering pharmaceuticals, e.g., orally, intranasally, intratracheally, or via injection routes, e.g., via intramuscular, intravenous, intraperiotenal or subcateneous routes. Preferably, the subject conjugates will be administered by injection, e.g., intraperitoneally, intravenously, intramuscularly, with the intravenous route being most preferred. The subject conjugates may be rendered into pharmaceutically acceptable form by the addition of known pharmaceutically acceptable carriers and excipients.

The subject polyamine transport inhibitor conjugates may also be administered in combination with DFMO. This will enable simultaneous inhibition of polyamine transport and synthesis and a determination of the in vivo effects thereof, e.g., in a particular disease condition, such as cancer or hypoxic pulmonary hypertension.

The most important in vivo application of the subject transport inhibitor conjugates will comprise their use as therapeutic agents. According to the present invention, conjugates may be synthesized which selectively inhibit the cellular uptake of any normally transported substance. Therefore, the subject conjugates may be used for the treatment of any disease condition wherein the cellular transport of a specific substance is required or is substantially involved in the disease condition.

Examples of other transported substances involved in disease conditions include amino acids, multiple drug resistance transporters such as p-glycoprotein (p-gp), transported polyproteins such as low density lipoprotein (LDL), neurotransmitters, serotonin, sugars, hormones saccharides, lipids, organic anions and cations, purines and steroids.

Moreover, given their size, selectivity and mode of action (at the cell membrane level) the subject conjugates should not produce any adverse effects since they are not internalized by cells and further do not appear to block cellular transport of non-targeted substances.

In the case of the exemplified polyamine transport inhibitor conjugates, these conjugates will be used therapeutically in the treatment of disease conditions wherein polyamine transport plays a substantial role in the disease condition. Disease conditions wherein increased polyamine transport is believed to exert a significant effect include diseases involving abnormal cell growth, differentiation and proliferation. Examples of such disease conditions include cancer, hypoxic pulmonary hypertension and related hypertensive pulmonary vascular diseases, intimal hyperplasia, secondary to balloon angioplasty ("restenosis"), intirmal hyperplasla which may result in prostnetic vascular graft failure, cerebral ischemic injury, hyperproliferative skin diseases such as psoriasis hypertensive diseases, gastric ulcers, leukemia systemic hypertension diseases, hyperoxic lung injury, and infectious diseases such as parasitic protozoan diseases.

The subject transport inhibitor conjugates when used as therapeutic agents may be administered via any known pharmaceutical mode of administration, e.g., orally, intravenously (via injection), intratracheally, or rectally. Preferably, the conjugates will be administered via injection, e.g., intravenously, intramuscularly, subcutaneously, or intraperitoneally.

The effective dosage of the subject conjugate will comprise dosages which are at least sufficient to inhibit transport of the particular targeted substance and which do not cause any adverse effects. Such dosages will vary dependent upon factors including the specific disease condition being treated, the particular conjugate being administered, its biological half-life, its ability to be delivered to the targeted site, etc. As discussed supra, the subject conjugates may further comprise a targeting moiety which enhances their selective delivery to targeted cells, e.g., tumor cells.

An effective therapeutic range will typically be sufficient to provide for polyamine concentrations ranging from 0.001 to 5000 µM, preferably ranging from about 0.01 µM to 2000 µM and most preferably ranging from about 0.01M to about 200 µM.

The subject transport inhibitor conjugates may be administered singularly or in combination with other drugs suitable in treating the particular disease condition. Also, the subject transport inhibitor conjugates may be administered together with substances which block synthesis of the particular transported substance so as to inhibit both the transport and synthesis of a transported compound involved in the particular disease condition. For example, the subject polyamine transport inhibitor conjugates may be administered in combination with DFMO, which is used to treat disorders wherein the cellular concentration of polyamines is involved in the particular disorder.

As discussed supra, an important therapeutic application of the subject polyamine transport inhibitor conjugates will involve the treatment of cancer since polyamine transport and synthesis is implicated in abnormal cell differentiation, growth and cell proliferation.

In the treatment of cancer, the subject polyamine inhibitors may further be administered in combination with known anti-neoplastic agents since data disclosed herein indicates that inhibition of polyamine transport may potentiate the efficacy of some anti-neoplastic agents, most likely because of inhibition of the MDR transporter system. Therefore, the use of the subject polyamine inhibitors in combination with one or more anti-neoplastic agents should result in enhanced anti-tumor activity.

Another important therapeutic application of the subject polyamine inhibitors comprises the inhibition of hypoxic pulmonary hypertension since data disclosed infra indicates that the subject conjugates inhibit fibronectin synthesis by pulmonary artery smooth muscle cells, the synthesis of which is believed to be implicated in pulmonary hypertension.

The following examples are offered to illustrate the present invention and should not be construed in any way as limiting its scope.

EXAMPLE ONE

Effect of Polyamine-Polyamine Conjugates and Polyamine-BSA Conjugates on Polyamine Uptake in Pulmonary Artery Smooth Muscle Cells It has been previously shown that cultured pulmonary artery smooth muscle cells, like may other cell types, express two different transport systems for polyamines; a "nonselective" carrier for putrescine, spermidine and spermine, and another carrier that is "selective" for spermidine and spermine. Based on this information, experiments were designed to determine whether the addition of the subject polyamine inhibitors, in concentrations ranging from 0–20 µM could block polyamine uptake by cultured pulmonary smooth muscle cells. Also, it was a further object of the experiment to determine whether the particular inhibitor could discriminate between the "nonselective" and "selective" polyamine transporter.

The two types of polyamine inhibitors tested in this example and the following examples comprise: (i) conjugates between bovine serum albumin (BSA) and either putrescine, spermidine or spermine using glutaraldehyde as a coupling agent; and (ii) large polyamine-polyamine polymeric conjugates of putrescine (Put-Put), spermidine (Spd-Spd) and spermine (Spm-Spm) using glutaraldehyde as a coupling agent. The molecular weight of the synthesized polyamine-BSA conjugates exceeded 65,000 daltons, whereas the polyaminepolyamine conjugates comprised a molecular weight in excess of 15,000 daltons.

Mass spectrum data has demonstrated that the most effective conjugate, polymeric spermine exhibited a molecular weight of about 25.5×0.5 KDa. Results of protron magnetic resonance, nuclear magnetic resonance, and mass spectral analyses indicate that the molecule exhibits a branched structure having relatively short extensions of repeating SPM-glut-SPM units off a longer polymeric SPM-glut-SPM backbone. The SPM moieties at the termination of each branch and backbone appear to be unconstrained and free to interact with the transporter binding sites. Also, these conjugates were found to retain biological stability for at least a month after synthesis.

Each of these polyamine-polyamine polymeric conjugates and the polyamine-BSA conjugates were added to pulmonary artery smooth muscle cell cultures at concentrations ranging from 0–20 µM, along with 3 µM of a specific $^{14}$C-polyamine and allowed to incubate for 30 minutes. After this 30 minute period the cell-associated radioactivity was then measured to determine the uptake of polyamine by the cell culture.

Figure 1B:
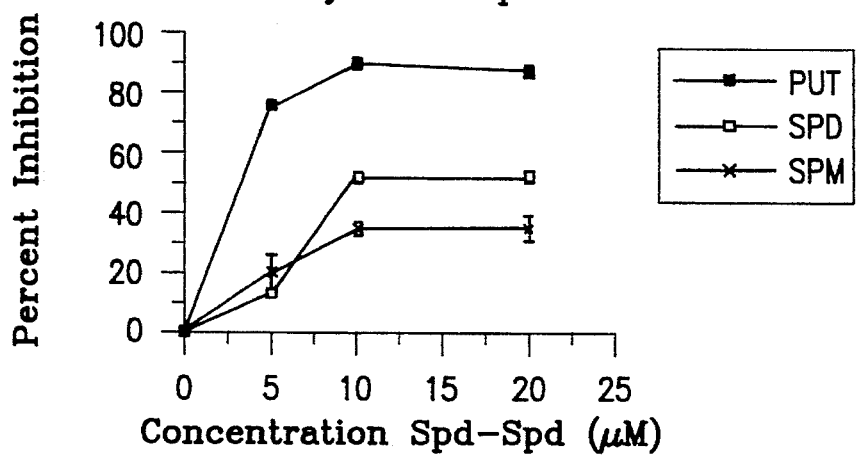
Figure 1C:
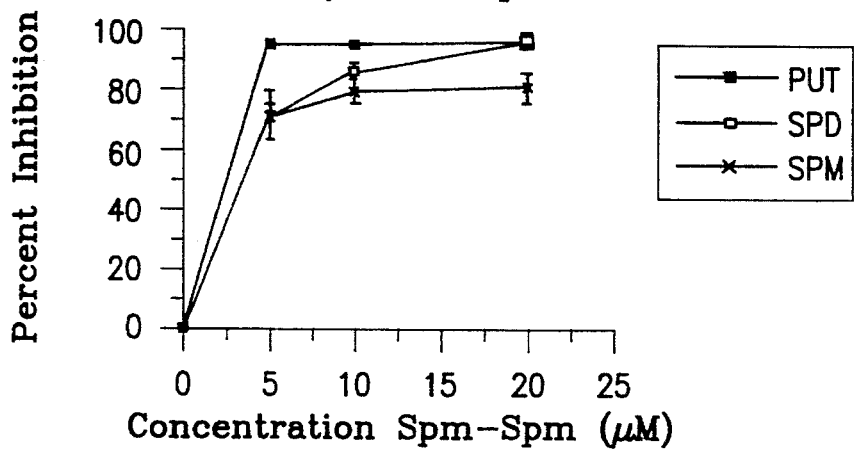
Figure 2A:
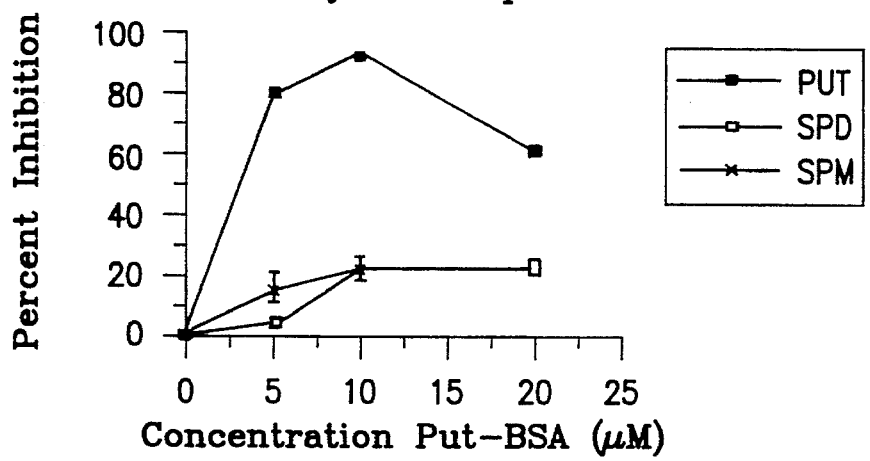
FIGS. 2A–2C: Effect of polyamine-BSA conjugates, BSA-putrescine (top), spermidine-BSA (middle), and spermine-BSA (bottom) on uptake of free $^{14}$C-polyamines in cultured pulmonary artery smooth muscle cells. Conjugates were added to the cultures simultaneously with 3 µM of a specific $^{14}$C-polyamine and allowed to incubate for 30 minutes after which the content of cell-associated radioactivity was determined. Each point is the mean ± the standard error of at least 6 replicates. These data indicate that the Put-BSA and Spm-BSA conjugates discriminate between the non-selective and selective spermidine/spermine transport systems and that the Spm-Spm conjugate effectively blocks the import of all three polyamines.
Figure 2B:
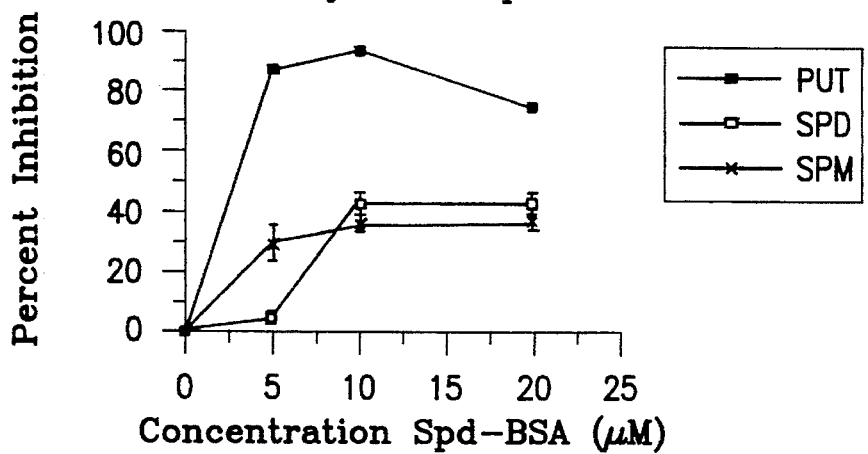
Figure 2C:
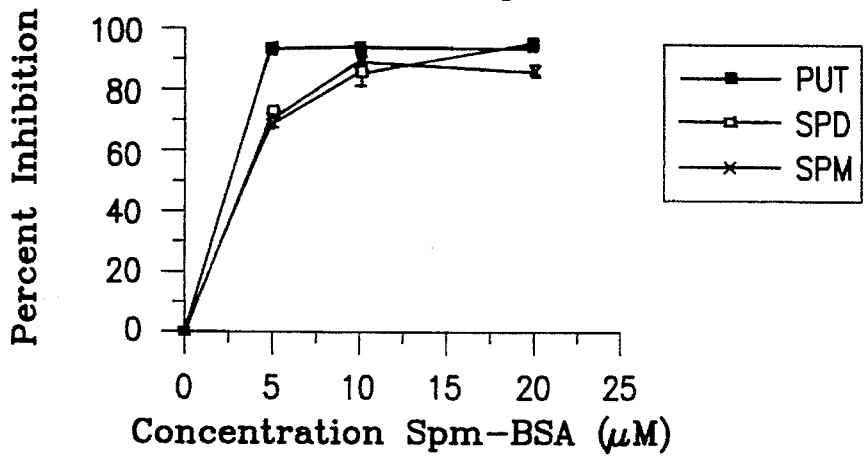

The results of these experiments are shown in FIGS. 1A–1C and 2A–2C. FIG. 1A–C depicts the effects of the polyamine-polyamine conjugates on polyamine uptake, whereas FIGS. 2A–2C depicts the effect of the polyamine-BSA conjugates on polyamine uptake.

It can be seen from FIG. 1A and 2A that both Put-Put and Put-BSA inhibited uptake of putrescine in the pulmonary artery cell cultures but failed to impair the uptake of spermidine and spermine.

By contrast, FIG. 1B and 2B demonstrate that both Spd-Spd and Spd-BSA inhibited uptake of putrescine and spermidine to a greater extent than spermine.

Also, the results contained in FIG. 1C and 2C indicate that both forms of the spermine inhibitor, Spm-Spm and Spm-BSA, inhibited uptake of putrescine, spermidine and spermine.

Control experiments were also conducted wherein the same concentrations of BSA were added to pulmonary artery smooth muscle cell cultures together with 3 µM of a specific $^{14}$C-polyamine and the cultures allowed to incubate for 30 minutes. Cell associated radioactivity was then measured. These results (not shown) indicated that free BSA (not conjugated to BSA) did not inhibit the uptake of putrescine, spermidine or spermine. Thus, the differential, concentration-dependent effects of the respective transport inhibitors on the uptake of the respective polyamines indicate that they prevent the uptake of polyamines by cultured pulmonary artery smooth muscle cell cultures and also that these inhibitors apparently interact selectively with the two polyamine transporters believed to exist in pulmonary artery smooth muscle cells as well as other cell types.

EXAMPLE 2

Effect of the Subject Polyamine Inhibitors of DFMO Stimulated Polyamine Uptake The present inventors have previously shown that the inhibition of polyamine synthesis in pulmonary artery smooth muscle cells with DFMO causes a compensatory increase in the activity of both the selective and non-selective polyamine transporters. Specifically, putrescine, spermidine and spermine uptake increases about 3–5 fold in comparison to cells not treated with the polyamine synthesis inhibitor. This phenomenon has been noted for numerous other cell types and probably explains why the therapeutic efficacy of DFMO is limited. Along with the induction of polyamine transport with DFMO, we have also found that culture of pulmonary artery smooth muscle cells in a hypoxic environment increases transport, however, not to the same extent as DFMO. This is important since hypoxia is a pathologically relevant stimulus for pulmonary hypertension.

Accordingly, similar experiments were conducted to determine if the induction of polyamine transport by DFMO and hypoxia would be prevented by the polyamine inhibitors of the present invention. The results of these experiments are shown in FIGS. 3A–3C and FIGS. 4A–4C. Specifically, putrescine-putrescine, spermidine-spermidine, spermine-spermine, putrescine-BSA, spermidine-BSA and spermine-BSA inhibitor conjugates were added in concentrations ranging from 0 to 20 μM to pulmonary artery smooth muscle cell cultures which had been treated with DFMO. DFMO treatment consisted of the addition of 1 mM of DFMO to the cultures followed by a 24 hour incubation period. The polyamine uptake was increased relative to control cells by about 350%.

After DFMO treatment and incubation, the respective conjugates were added in amounts ranging from about 0 to 20 μM simultaneously with 3 μM of a specific $^{14}$C-polyamine and the cells allowed to incubate for 30 minutes. After incubation, the content of cell associated radioactivity was determined. The results in both FIGS. 3A–3C and FIG. 4A–4C indicate that the subject polyamine conjugates inhibit both transport systems in cells wherein polyamine uptake has been stimulated by inhibition of de novo polyamine synthesis.

Similar experiments were conducted to determine the effects of the subject inhibitor conjugates on hypoxic pulmonary artery smooth muscle cells. These results are not shown, however, the results were identical to those obtained in the DFMO-treated cells. The observed results indicated that both types of inhibitors suppressed polyamine uptake in an identical manner to their actions in control cells in the absence of DFMO or hypoxia.

Figure 3A:
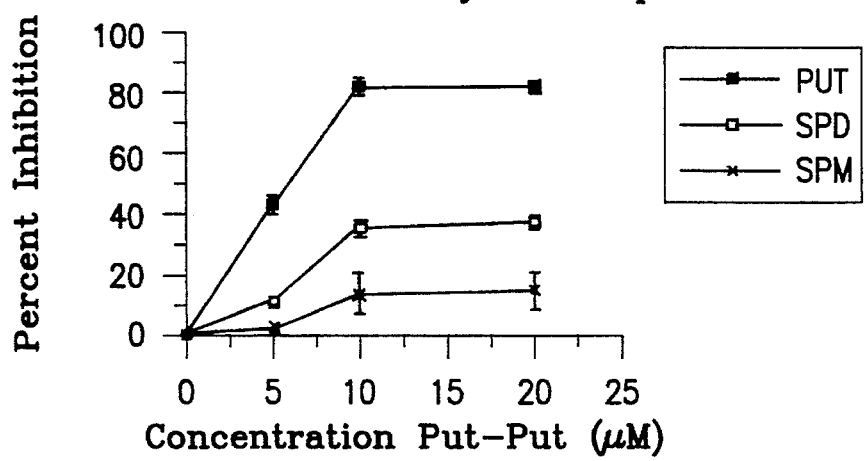
FIGS. 3A–3C: Effect of polyamine-polyamine conjugates, putrescine-putrescine (top), spermidine-spermidine (middle), and spermine-spermine (bottom) on uptake of free $^{14}$C-polyamines in cultured pulmonary artery smooth muscle cells treated with DFMO. DFMO treatment (1 mM for 24 hours) increased polyamine uptake approximately 350% relative to control cells. Conjugates were added to the cultures after DFMO treatment and simultaneously with 3 µM of a specific $^{14}$C-polyamine and allowed to incubate for 30 minutes after which the content of cell-associated radioactivity was determined. Each point is the mean ± the standard error of at least 6 replicates. These data indicate that polyamine conjugates inhibit both transport systems in cells with polyamine uptake stimulated by inhibition of de novo polyamine synthesis.
Figure 3B:
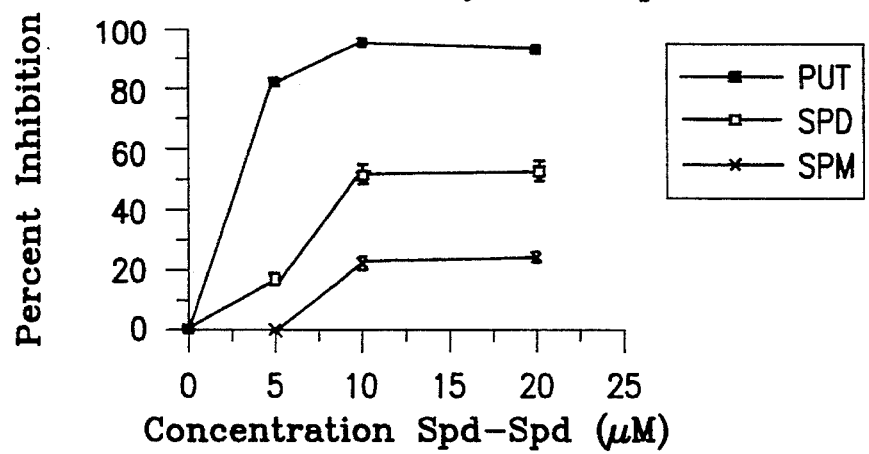
Figure 3C:
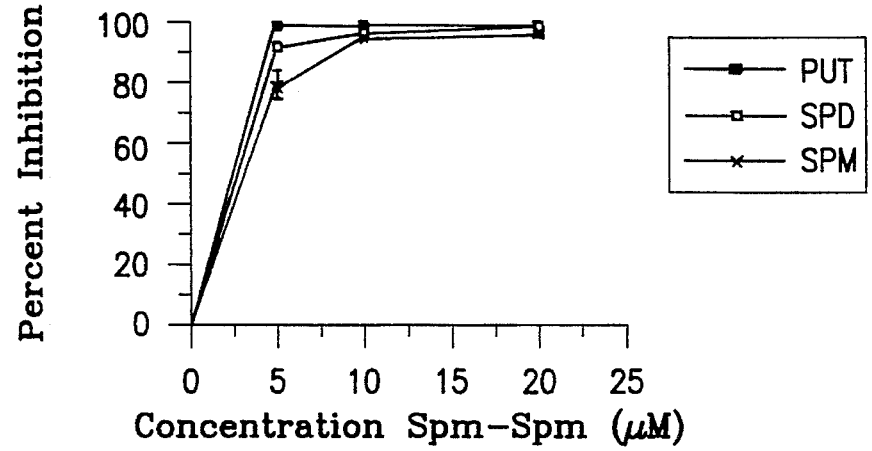
Figure 4A:
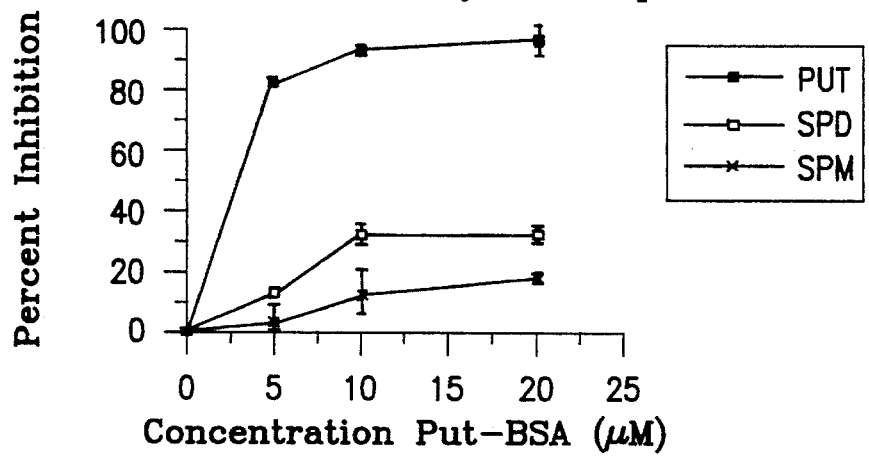
FIGS. 4A–4C: Effect of polyamine-BSA conjugates, putrescine-BSA (top), spermidine-BSA (middle), and spermine-BSA (bottom) on uptake of free $^{14}$C-polyamines in cultured pulmonary artery smooth muscle cells treated with DFMO. DFMO treatment (1 mM for 24 hours) increased polyamine uptake approximately 350% relative to control cells. Conjugates were added to the cultures after DFMO treatment and simultaneously with 3 µM of a specific $^{14}$C-polyamine and allowed to incubate for 30 minutes after which the content of cell-associated radioactivity was determined. Each point is the mean ± the standard error of at least 6 replicates. These data indicate that polyamine-BSA conjugates inhibit both transport systems in cells with polyamine uptake stimulated by inhibition of de novo polyamine synthesis.
Figure 4B:
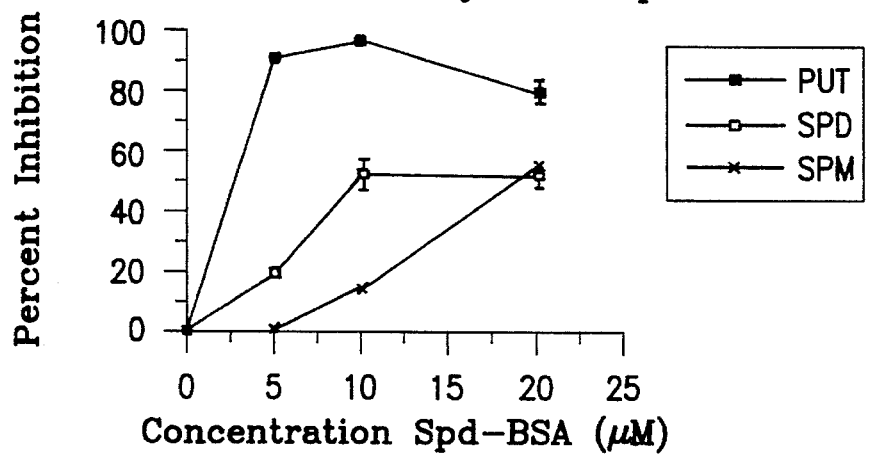
Figure 4C:
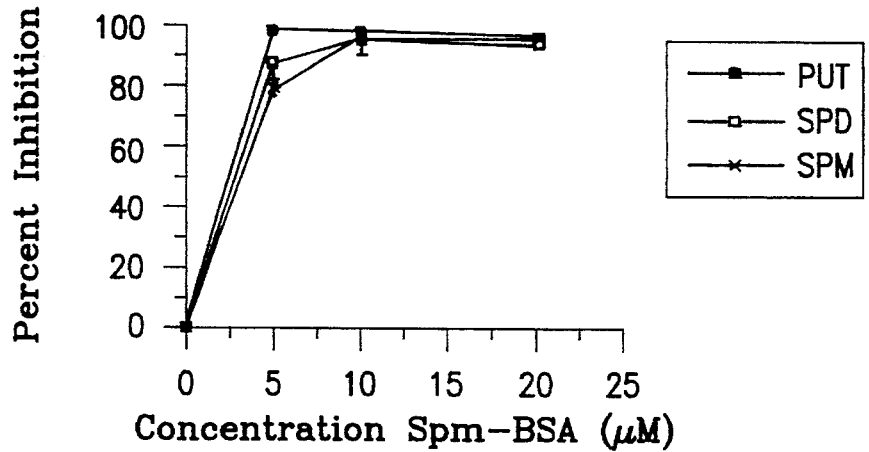

The putrescine conjugates inhibited accumulation of putrescine to a greater extent than spermine and spermidine in DFMO cells (as shown in FIG. 3A and 4A), while the spermidine and spermine conjugates inhibited uptake of all polyamines (as shown in FIGS. 3B, 3C, 4B and 4C). Thus, the inhibitors are effective and retain their selectivity even under conditions of augmented polyamine transport.

EXAMPLE 3

The Effect of the Subject Polyamine Conjugates on Cultured Bladder Cancer Cells The previous examples related to the effects of the subject conjugates on pulmonary artery smooth muscle cells. To prove that these phenomena were not cell specific and that the invention has broad applicability for other cell types, in particular pathologically-relevant cells, the following experiments were conducted.

Specifically, the effect of the subject spermine-spermine conjugates on two types of cultured bladder cancer cells was examined, the first designated DXE, are resistant to anti-tumor drugs and the second designated MESSE are sensitive to such anti-tumor agents. Spermine-spermine conjugates were selected since the available data indicates that this conjugate is an effective and potent polyamine transport inhibitor for both polyamine transport systems. As shown in Table 1 set forth below, it was found that 20 μM of the spermine-spermine conjugate reduced uptake of spermidine in both cell populations. Thus, the results indicate that the subject conjugates should have both clinical and therapeutic for applicability in inhibiting polyamine transport by cancer cells. Also, the subject conjugates should provide utility in vivo and in vitro for studying the relatedness of the polyamine transport system and the multi-drug resistance transport system.

TABLE 1

Impact of Spm-Spm Conjugate on Spermidine Uptake by Drug-sensitive (MESSE) and Drug-resistant (DXE) Human Bladder Cancer Cells in Culture.
Spermidine Uptake (μM/30 min/μg protein)

| Cell Type | Control | +20 μM Spm-Spm |
|---|---|---|
| MESSE | 5.53 ± 0.35 | 0.33 ± 0.14 |
| DXE | 1.00 ± 0.03 | 0.32 ± 0.02 |

EXAMPLE 4

Effect of the Subject Conjugates on Uptake of Amino Acids

As discussed supra, there are some parallels between the transport of polyamines and amino acids. Accordingly, the present inventors considered the possibility that the subject polyamine transport inhibitors may not be selective, i.e., they may inhibit the uptake of naturally occurring amino acids as well as polyamines.

To prove that this was not occurring, the effect of the subject polyamine-BSA and polyamine-polyamine conjugates on the uptake of the non-metabolizable amino acids, specifically methyl amino isobutyric acid and lysine was examined in cultured pulmonary artery smooth muscle cells. These amino acids were selected because lysine is positively charged like the subject polyamines and also because both these amino acids use different transport systems which are distinct from the polyamine transport system.

The results of this experiment are found in Tables 2A and 2B set forth on the following page:

TABLE 2A

Impact of Polyamine-Polyamine Conjugates (20 μM) on Uptake of Non-Polyamine Amino Acids in Cultured Pulmonary Artery Smooth Muscle Cells
PERCENT CONTROL UPTAKE

| Amino Acid | Put-Put | Spd-Spd | Spm-Spm |
|---|---|---|---|
| MAIBA* | | | |
| 2.5 μM | 106 ± 4 | 114 ± 5 | 126 ± 5 |
| 5.0/μM | 103 ± 6 | 106 ± 5 | 117 ± 12 |
| Lysine | | | |

TABLE 2A-continued

Impact of Polyamine-Polyamine Conjugates (20 µM) on Uptake of
Non-Polyamine Amino Acids in Cultured Pulmonary
Artery Smooth Muscle Cells
PERCENT CONTROL UPTAKE

| Amino Acid | Put-Put | Spd-Spd | Spm-Spm |
|---|---|---|---|
| 2.5 µM | 105 ± 4 | 103 ± 13 | 99 ± 11 |

*MAIBA: methylaminoisobutyric acid

TABLE 2B

Impact of Polyamine-BSA Conjugates (20 µM) on Uptake of
Non-Polyamine Amino Acids in Cultured Pulmonary
Artery Smooth Muscle Cells
PERCENT CONTROL UPTAKE

| Amino Acid | Put-Put | Spd-Spd | Spm-Spm |
|---|---|---|---|
| MAIBA* | | | |
| 2.5 µM | 121 ± 2 | 115 ± 6 | 198 ± 8 |
| 5.0 µM | 126 ± 10 | 120 ± 7 | 129 ± 11 |
| Lysine | | | |
| 2.5 µM | 113 ± 18 | 100 ± 8 | 109 ± 8 |

*MAIBA: methylaminoisobutyric acid

These results demonstrate that neither the polyamine-polyamine conjugates or the polyamine-BSA conjugates impaired the uptake of these two amino acids. Thus, this provides further evidence that the subject polyamine transport inhibitors are selective for inhibiting polyamine transport. This is further supported by the fact that even within the different polyamine conjugates there are variable effects on uptake of the different polyamines, e.g., Put-Put and Put-BSA inhibited the uptake of putrescine but not spermine or spermidine.

EXAMPLE 5

Determination as to Whether the Subject Polyamine Conjugates are Internalized by Treated Cells The inventors considered the possibility that the subject inhibitors do not block polyamine transport, but rather merely substitute for the naturally-occurring polyamines and are thereby transported into the cell where they may exert some biological activity. However, this was considered highly improbable given that the molecular weight of the subject conjugates which for both classes of inhibitors is respectively in excess of 15,000 and 65,000 daltons.

Two strategies were devised to determine whether the conjugates internalized into the cell or remained confined to the cell surface. In the first experiment, the inventors made use of their previous observation that the operation of the polyamine transporter is temperature sensitive. At low temperature the transporter is inoperative and polyamines associated with the cell are bound non-specifically to the membrane. Thus, it was reasoned that if the subject inhibitors access the cell interior via the polyamine transporter, then there should be substantial differences between the cell content of the inhibitors at normal and low-temperature conditions. Therefore, radioactive polyamine-polyamine conjugates were synthesized using radioactive polyamines (analogous to the method for assessing polyamine uptake in the previous examples). After incubation of pulmonary artery smooth muscle cells with the radioactive labelled polyamine-polyamine conjugates at 4° and 37° C., the cell-associated radioactivity was then determined. In accord with the inventors' expectations, there were no discernable differences in the content of cell-associated radioactivity between cells at low and normal temperature (data not shown).

Also, a second experiment was conducted to determine whether the inhibitors internalize cells using confocal microscopy, using methods such as an described in Fisher et al, *Nucl. Acids Res.*, 21, 3857–3865, 1993; Petroll et al, *J. Microsc.* 170, 213–219, 1993; and Schipper et al, *Exp. Cell Res.*, 207, 62–67, 1993. The BSA portion of a spermine-BSA conjugate was labelled with the fluorescent molecule rhodamine and confocal. Microscopy was then used to determine the cellular localization of the conjugate.

This technique examines the cells much like a CAT scan examines the human body. Essentially, the microscope takes pictures of discrete sections through the vertical dimension of a cell, the uppermost of which comprises the cell membrane, whereas a mid-level picture would likely capture the cell nucleus, etc. Using this technique, it was found (results not shown) that all of the cell fluorescence was localized to the cell membrane and that no fluorescence would be detected in any interior portion of the cell.

Based on both the temperature-dependent experiments and the fluorescence studies using confocal microscopy, it is believed by the present inventors that the subject polyamine transport inhibitors act at the level of the cell membrane and do not access the cell interior.

EXAMPLE 6

Biological Effects of the Subject Polyamine Inhibitors

In order to determine the biological effects of the subject inhibitors on cells, several experiments were conducted. For example, it was observed that treatment of pulmonary artery smooth muscle cells with 30 µM of the subject conjugates did not result in exclusion of the vital stain tryptan blue. This provides further evidence that the conjugates are not overtly toxic.

Also, the effects of Spm-Spm on the induction of fibronectin synthesis by hypoxic in pulmonary artery smooth muscle cells was determined. This experiment was effected because hypoxic pulmonary hypertension is accompanied by the deposition of large quantities of fibronectin around pulmonary arteries. Therefore, there is some belief by researchers, including the present inventors, that the increased deposition of this protein may be an important cause of the sustained elevation in pulmonary arterial blood pressure. Also, hypoxia seems to cause pulmonary hypertension by a mechanism related to increased polyamine transport rather than increased de novo polyamine synthesis.

The availability of the subject polyamine transport inhibitors therefore provided an opportunity to test the hypothesis that hypoxia evokes synthesis and release of a pathologically-relevant protein by a polyamine transport-dependent mechanism.

The results of this experiment are contained in Table 3.

TABLE 3

Impact of DFMO and Spm-Spm Conjugate on Hypoxia-induced
Fibronectin Synthesis in Cultured Pulmonary
Artery Smooth Muscle Cells
Fibronectin Synthesis (OD/mg protein)

| Exptl. Group | Control | DFMO | Spm-Spm | DFMO + Spm |
|---|---|---|---|---|
| Normoxic | 0.08 | 0.07 | 0.05 | 0.04 |
| Hypoxic | 0.12 | 0.09 | 0.06 | 0.05 |

In the control (non-hypoxic cells), inhibitors of de novo polyamine synthesis with DFMO failed to reduce the accumulation of fibronectin in the culture medium. By contrast, inhibition of polyamine transport with the Spm-Spm conjugate resulted in a substantial reduction of accumulation of fibronectin which was not suppressed by the addition of DFMO. This is consistent with the inventors' belief that de novo synthesis of polyamines is not involved in the response to hypoxia. Moreover, the results indicate that the Spm-Spm conjugate prevent a biological response (increased fibronectin accumulation) believed to be strongly involved in hypoxic pulmonary hypertension.

Also, the effects of the subject polyamine inhibitors using the transport of an anti-tumor drug (viablastine) by cultured human bladder cancer cells was examined. It is known that cancer cells express a specialized membrane pump called the "Multiple Drug Resistance" (MDR) transporter. This comprises a therapeutically significant system since it enables tumor cells to become resistant to anti-tumor drugs by pumping an anti-tumor drug out of the cell interior.

One MDR transporter has been identified by previous researchers which comprises 12 discrete domains that span the cell membrane. Only about a half dozen of such 12-domain membrane spanning type proteins are known in the art, with one being the putrescine transporter isolated from bacteria. Accordingly, the present inventors postulated that the MDR pump and the polyamine transport system may be functionally related, particularly given the fact that both transport systems are highly expressed in tumor cells.

To test this hypothesis, experiments were conducted to determine whether or not inhibitors of the MDR transporter would decrease polyamine uptake and, conversely, if inhibition of polyamine import with the subject polyamine conjugates would attenuate the MDR pathway, thereby increasing the cellular content of anti-tumor drugs.

In the first study, the effects of two agents known to inhibit the MDR, i.e., verapamil and cyclosporin, on polyamine transport by cultured pulmonary artery smooth muscle cells was assessed. The results obtained indicate that both agents suppress polyamine transport by about 50–75% (data not shown).

In the second study, culture of the above-noted MESSE and DXE human bladder cancer cells were treated with Spm-Spm and the tumor cell content of the anti-cancer drug vinblastine was then measured.

As shown in Table 4A set forth below, Spm-Spm provided modest, but significant increases in the tumor cell content of vinblastine. The data contained in Table 4B, set forth on the following page, on the further suggest that the effect of Spm-Spm on the retention of vinblastine by tumor cells is dramatically more pronounced when the cells are rendered hypoxic (a condition which may mimic that of cells comprised in the center of a solid tumor). This may be explained by the presence of another type of MDR transport system.

TABLE 4A

Impact of Spm-Spm Conjugate on Vinblastine Uptake by Drug-sensitive (MESSE) and Drug-resistant (DXE)
Human Bladder Cancer Cells in Culture
Vinblastine Uptake (dpm/30 min/µg protein)

| Cell Type | Control | +20 µM Spm-Spm |
|---|---|---|
| MESSE | 9.7 ± 0.3 | 13 ± 0.3 |
| DXE | 10 ± 0.2 | 14 ± 0.1 |

TABLE 4B

Impact of Spm-Spm Conjugate on Vinblastine Uptake by Drug-sensitive (MESSE) and Drug-resistant (DXE)
Human Bladder Cells Cultured in an Hypoxic Environment
Vinblastine Uptake (dpm/30 min/µg protein)

| Cell Type | Control | ± 20 µM Spm-Spm |
|---|---|---|
| MESSE | 6.2 ± 0.6 | 8.3 ± 0.7 |
| DXE | 3.2 ± 0.7 | 8.3 ± 1.3 |

These results are extremely exciting since they provide further evidence regarding the link between the MDR and polyamine transport pathways. Also, they expand the potential utility of the subject polyamine transport inhibitors as anti-neoplastic agents. In particular, administration of the subject inhibitors to cancer subjects should prevent cancer cells by inhibiting uptake of polyamines required for abnormal cell proliferation.

Also, when the subject inhibitors are administered in conjunction with anti-cancer agents they should enhance their efficiency by preventing their MDR-driven export from tumor cells.

EXAMPLE 7

Effect of Polyamine-conjugates on Cultured
Cultured Human Uterine Sarcoma and Leukemia
cells[1]

Figure 5:
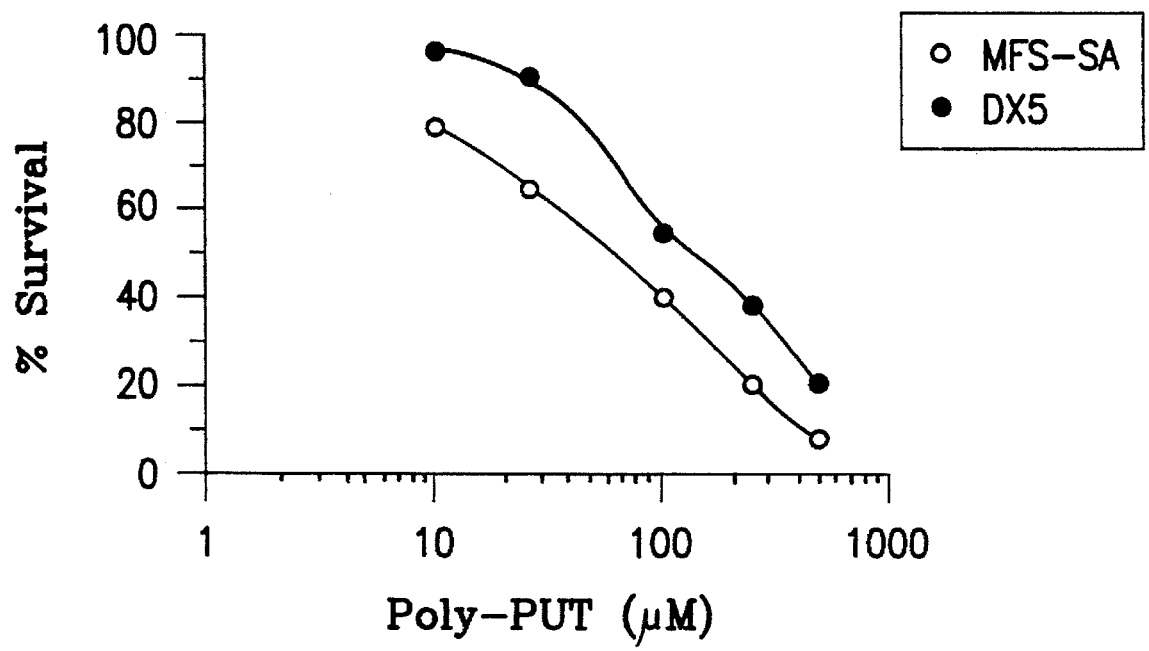
FIG. 5: Concentration-dependent cytotoxicity of Poly-PUT conjugate in a parental lineage of human uterine sarcoma cells (MES-SA) and variants (DX5) expressing drug resistance secondary to expression of the p-glycoprotein. Each point is the mean ± SEM of 3 replicates.

Cytotoxicity was assessed using the MTT assay in MES-SA and DX5 uterine sarcoma cell lines after a 24 hours exposure to ascending concentrations of the putrescine polymeric conjugates (poly-PUT conjugates) or its vehicle. As shown in FIG. 5, the poly-PUT conjugate evoked concentration-dependent lethality in MES-SA and DX5 cells. Concentrations of poly-PUT associated with 50% cytotoxicity ($IC_{50}$) were 60±12 and 200±20 µM in MES-SA and DX5 cells, respectively. The cytotoxic effects of a polymeric conjugate of spermine (poly-SPM), which suppresses transport of all three polyamines in smooth muscle cells, in both MES-SA and DX5 cells as well as K567 Human leukemia cells and their MDR-positive variants R7 cells are shown in Table 5. Similar to the impact of poly-PUT, poly-SPM also is cytotoxic in both cancer cells lines, with the MDR-positive variants being slightly more resistant. There are at least several interesting aspects regarding these observations. First, they demonstrate that the polyamine-conjugates exhibit antineoplastic activity in two human cancer cells lines. Second, the finding that the SPD-conjugate is somewhat more potent than the PUT conjugate is consistent with previous data indicating that the former is more effective in blocking polyamine uptake in bovine pulmonary artery smooth muscle cells (PASMCs). Further studies with the SPM-conjugate are planned since this compound appears to be the most potent polyamine transport inhibitor in pulmonary artery smooth muscle cells (PASMCs) by virtue of its activity against both of the putative uptake pathways. Finally, the nearly 3-fold difference in sensitivity between DX5 and MES-SA cells suggests that the presence of the MDR transporter could be a determinant of polyamine transport activity and the attendant sensitivity of cancer cells to killing by polyamine transport inhibitors. This will be addressed in further research.

The Conjugate Concentrations for experiments 7–13 were determined based on the molecular weight of free polyamines and not the molecular weight of the conjugates. For example, Poly-SPM concentrations would be 71 times lower if they were determined based on molecular weight of Poly-SPM (25 KDa) rather than SPM which is around 350.

TABLE 5

Poly-SPM conjugate Cytotoxicity in Parental and MDR cells

| Cell Line | IC50 (μM) | Resistance |
|---|---|---|
| MES-SA | 37 ± 10 | 4.5-fold |
|  | 170 ± 4.0 |  |
| K567 | 43 ± 5 |  |
| R7 | 137 ± 20 | 3.2-fold |

EXAMPLE 8

Polyamine Conjugates Inhibit Polyamine Uptake and Reduce Cell Polyamine Contents in Human Cancer Cells Additional studies were conducted to determine whether MES-SA and DX5 cell lines express a polyamine transport system, and, if so, whether this system(s) was inhibited by the poly-PUT and poly-SPM conjugate. We focused our efforts on comparisons between the PUT and SPM conjugates because these compounds appeared to discriminate between the selective and nonselective pathways in bovine pulmonary artery smooth muscle cells. In the current studies, $^{14}$C-SPD was added in concentrations of 3 μM and cells were incubated for 30 minutes at selected temperatures (4° and 37° C). The cells were rinsed with Hanks buffer, digested for 1 hour in 1N NaOH, and cell-associated radioactivity was determined. $^{14}$C-SPD uptake rate was normalized to protein content. Specific, carrier-mediated polyamine uptake was calculated subtracting the total polyamine uptake, determined at 37° C., from the non-specific polyamine burden determined at 40° C. As shown in Table 6 MES-SA and DX5 express a polyamine transport system as evidenced by substantial temperature-dependent polyamine accumulation. Addition of 20 μM SPM-SPM conjugate reduced polyamine transport in MES-SA and DX5 cells by 10 and 3 fold, respectively. These results indicate that the polyamine conjugates are effective in blocking polyamine transport in uterine sarcoma cells, which is consistent with our previous experience in bovine PASMCs. It also is noteworthy that the uptake of SPD, as assessed at a single concentration (3 μM), is substantially less in the DX5 cell line(1±0.03) than in control (5.5±0.35). The reasons for this are unclear, but it is hypothesized that the presence of the MDR confers greater resistance to polyamine uptake blockade by promoting compensatory increases in the activity of de novo pathways of polyamine synthesis.

TABLE 6

Impact of poly-PUT and poly-SPM Conjugates on $^{14}$C-SPD Uptake by MDR-negative (MES-SA) and MDR-positive (DX5) Human Uterine Sarcoma Cells in Culture
% Specific Spermidine Uptake

| Cell Line | Control | +20 μM poly-PUT | +20 μM poly-SPM |
|---|---|---|---|
| MES-SA | 100 | 84 ± 2.4 | 15.6 ± 0.6 |
| DX5 | 100 | 57 ± 3.3 | 6.2 ± 0.13 |

EXAMPLE 9

Effect of Polyamine Conjugates or Polyamine Transport By Human Leukemia Cells K567 leukemia cells and their MDR positive variant were suspended at a density of 25×10$^4$ cells/ml in serum free medium. 1 μM of $^{14}$C-SPD was added and the cells were incubated at 37° C. for 30 minutes. Incubation was terminated by rapidly chilling the cells on ice followed by centrifugation of 6000 RPM for 5 minutes at 4° C. The cells were washed in ice-cold Tris buffer and centrifugated. The pellet was lysed for 1 hour in 1N NaOH, and cell accumulated radioactivity was determined. $^{14}$C-SPD uptake rate was normalized to protein content. Both the K567 human leukemia cell line and its MDR positive variant R7 expressed the polyamine transport system as shown in Table 7. Presence of 20 μM poly-SPM almost completely blocked polyamine transport in K567 cells and its MDR variant R7.

TABLE 7

Impact of poly-SPM Conjugates on $^{14}$C-SPD Uptake by MDR-negative (K567) and MDR-positive (R7) Human Leukemia Cell Lines
Specific Spermidine Uptake
Pmole/min/mg protein

| Cell Line | Control | +20 μM poly-SPM |
|---|---|---|
| K567 | 77.3 ± 1.5 | 0.7 ± 0.03 |
| K567/R7 | 27.0 ± 0.5 | 0.73 ± 0.09 |

EXAMPLE 10

To determine if the cytotoxicity and inhibition of polyamine transport evoked by the polyamine conjugates was,associated with depletion of cell polyamine contents, additional experiments were conducted which used HPLC to measure contents of PUT, SPD, and SPM in human uterine sarcoma and leukemia cells in the presence of poly-SPM, DFMO, and combined treatment with poly-SPM and DFMO. The latter combination was tested to determine if blockade of both transport and synthesis would promote greater decreases in polyamine content than either intervention alone. As shown in Table 8, poly-SPM was effective in decreasing contents of all polyamines in all cells, while DFMO caused modest depletion of SPD but not SPM. This is a significant enlightening observation; numerous reports have commented that DFMO fails to reduce SPM levels, and this has been invoked as an additional explanation of the relatively unimpressive cytotoxicity of DFMO. Indeed, DFMO at 1 mM concentration was not toxic to either MES-SA or K562 cells or their MDR-positive variants. By contrast, poly-SPM, which decreases SPM contents along with the other polyamines is highly toxic to all cells. It was also observed that the effect of poly-SPM+DFMO in combination on cell polyamine contents tended to be greater than either agent alone, thus highlighting the interactive roles of transport and synthesis in governing polyamine contents. Further studies are planned to obtain further information regarding interactions between these pathways and their suitabilities as pharmacologic targets. It is potentially significant that the impact of poly-SPM on polyamine contents in the MDR-positive cells was somewhat less impressive than in the parental lines. This finding may have implications for mechanisms by which polyamine transport and MDR activity are interactive processes.

TABLE 8

Cellular Polyamine Content (pmoles/mg protein) in MDR-negative (MES-SA, K562) and MDR-positive (DX5, K562/R7) Human Cancer Cells

| Treatment | PUT | SPD | SPM | PUT | SPD | SPM |
|---|---|---|---|---|---|---|
| | | MES-SA | | | DX5 | |
| Control | 2172 | 11913 | 6477 | 1195 | 9685 | 6202 |
| DFMO (1 mM) | ND | 6100 | 8824 | ND | 4191 | 6831 |
| Poly-SPM (20 μM) | 722 | 6845 | 4368 | ND | 7496 | 6089 |
| Poly-SPM + DFMO | ND | 3477 | 4167 | ND | 5136 | 5635 |
| | | K562 | | | K562/R7 | |
| Control | 5331 | 22996 | 10987 | 6902 | 26372 | 12559 |
| DFMO (1 mM) | ND | 15791 | 17024 | ND | 15809 | 15083 |
| Poly-SPM (20 μM) | ND | 3234 | 2384 | 1042 | 6133 | 4779 |
| Poly-SPM + DFMO | ND | 2412 | 2312 | ND | 2142 | 1793 |

Collectively, these findings indicate that the cytotoxicity of polyamine conjugates in human tumor cells is associated with depressed transmembrane polyamine transport and decreased cell polyamine contents. It is therefore reasonable to conclude that the decreased cell polyamine content is the proximate mechanism of cytotoxic action of the polyamine conjugates. We also have observed interesting differences in the impact of polyamine transport blockade and kinetics of polyamine transport between MDR-positive and -negative cell lines, which suggest that there exist pharmacologically-significant interactions between these transport systems.

EXAMPLE 11

Modulation of MDR Activity by Polyamine Transport and Synthesis Inhibition in Human Uterine Sarcoma Cells Complimentary experiments were conducted to determine whether the polyamine uptake inhibitors differentially affected the cytotoxicity and cellular uptake of vinblastine in MDR-negative and MDR-positive uterine sarcoma cells. Making use of the fact that vinblastine is a well known substrate for the MDR transporter, we reasoned that if polyamine uptake blockade suppressed MDR activity, then this should be reflected as a decrease in the resistance of MDR-positive cells to vinblastine-induced killing in concert with an increase in the cellular retention of the alkaloid. The MTT assay was used to quantify the $IC_{50}$ for vinblastine cytotoxicity in MES-SA and DX5 cells in the presence and absence of treatment with 100 μM poly-PUT. The calculation of cytotoxicity in these experiments accounted for the lethality associated with use of the conjugate alone. As shown in Table 9, DX5 cells were resistant to vinblastine cytotoxicity relative to the parental MES-SA cells and retained less vinblastine. The PUT-conjugate had little effect on the $IC_{50}$ for vinblastine cytotoxicity in MES-SA, but caused a 60-fold decrease in the MDR-positive DX5 line. Similarly, while the baseline vinblastine content in DX5 cells was, as expected, less than in MES-SA cells, the conjugate increased drug retention in the MDR-negative cells by a mere 50% while vinblastine retention was increased over 200% in the MDR-positive line. These findings provide pharmacologic evidence that the MDR pathway and polyamine transport are functionally interactive in this human uterine sarcoma cell line. Similar results were generated with the use of another substrate of MDR transporter, Taxol. Treatment with 100 μM poly-SPM increased the accumulation of Taxol in DX5 cells, but not MES-SA. Poly-SPM also caused a decrease in IC50 for Taxol in DX5 without significant effect on MDR-negative MES-SA cell line (data not shown).

TABLE 9

Impact of Poly-PUT Conjugate on Vinblastine Cytotoxicity and Uptake by MDR-negative (MES-SA) and MDR-positive (DX5) Human Uterine Sarcoma Cells

| | $IC_{50}$ (μM) | | $^{14}$C-Vinblastine Content (dpm/30/min/μg protein) | |
|---|---|---|---|---|
| Cell Line | Control | +100 μM PUT-Conjugate | Control | +100 μM PUT-Conjugate |
| MES-SA | .005 | .007 | 6.2 ± 0.6 | 8.3 ± 0.7 |
| DX5 | 0.6 | .116 | 3.2 ± 0.7 | 8.3 ± 1.3 |

EXAMPLE 12

Effect of DFMO on Polyamine Transport in MDR-negative (MES-SA) and MDR-positive (DX5) Human Uterine Sarcoma Cells In many cells, DFMO increases polyamine transport. This is believed to be a compensatory mechanism that protects these cells from polyamine depletion. Indeed, in the preliminary studies described supra, DFMO was less effective than transport blockade in reducing cell polyamines and in causing cell death. The present invention accordingly concluded that the induction of transport by DFMO would be a useful strategy for further experiments. Indeed, if MDR activity is linked to polyamine transport rate, then the actions of DFMO on MDR activity should be opposite to those of the transport inhibitors, despite the fact that both DFMO and the transport inhibitors have qualitatively similar effects on cell polyamine contents. In other words, while polyamine conjugates decrease MDR activity, DFMO should promote an increase in activity which reduces cytotoxic drug content and decreases drug-induced lethality. We therefore examined the impact of DFMO on polyamine transport rate and on vinblastine accumulation and cytotoxicity in MES-SA and DX5 cells. As shown in Table 10, it was found that 24 hours' treatment with DFMO caused slight increases in both PUT and SPD transport rate in DX5 cells but, surprisingly, not in MES-SA cells. These results suggest that cells expressing the MDR phenotype exhibit a DFMO-inducible polyamine transporter that may not be present in MDR-negative cells.

TABLE 10

Effect of DFMO on Polyamine Transport in MDR-negative (MES-SA) and MDR-positive (DX5) Human Uterine Sarcoma Cells $^{14}$C-Polyamine uptake (pmoles/min/mg protein)

| Cell Line | CONTROL | | DFMO (1 mM) | |
|---|---|---|---|---|
| | PUT | SPD | PUT | SPD |
| | SPD | | | |
| MES-SA | 0.7 ± 0.06 | 7.6 ± 0.2 | 0.67 ± 0.01 | 7.3 ± .06 |
| DX5 | 0.8 ± 0.05 | 1.4 ± 0.2 | 1.1 ± 0.04 | 1.6 ± .08 |

EXAMPLE 13

Effect of DFMO on Vinblastine Accumulations in MDR-negative (MES-SA) and MDR-positive (DX5) Human Uterine Sarcoma Cells DFMO, as predicted, decreased vinblastine accumulation in DX5 cells but not in the parental line, MES-SA (Table 11). In a companion study, MES-SA cells exhibited the expected sensitivity to vinblastine relative to DX5, characterized by $IC_{50}$ values of 0.005 μM and 0.5 μM, respectively. Importantly, DFMO treatment failed to affect the $IC_{50}$ value for vinblastine in MES-SA cells but engendered complete resistance in DX5 cells to vinblastine, at least in concentrations up to 5 μM. Thus, DFMO which increases polyamine transport in DX5 cells also appears to increase MDR activity and render MDR-positive cells even more resistant to the cytotoxic effects of vinblastine.

TABLE 11

Effect of DFMO on Vinblastine Accumulation in MDR-negative (MES-SA) and MDR-positive (DX5) Human Uterine Sarcoma Cells
$^3$H-Vinblastine Content (pmoles/mg protein)

| Cell Line | CONTROL | DFMO (1 mM) |
|---|---|---|
| MES-SA | 825 ± 20 | 840 ± 28 |
| DX5 | 290 ± 10 | 195 ± 8 |

What is claimed is:

1. A method for inhibiting the cellular uptake of a polyamine or polyamines comprising contacting cells which are capable of actively transporting said polyamine or polyamines with a transport inhibitory effective amount of an inhibitor which comprises a polymer or copolymer wherein the repeating units comprise said polyamine or polyamines.

2. The method of claim 1 wherein the repeating units of the transported substance are covalently attached by a coupling agent.

3. The method of claim 2 wherein the coupling agent is glutaraldehyde.

4. The method of claim 1 wherein said polymer or copolymer comprises a polyamine selected from the group consisting of putrescine, spermine and spermidine.

5. The method of claim 1 wherein said polymer of the transported substance comprises a molecular weight ranging from 15,000 to 100,000 daltons.

6. The method of claim 1 wherein the polymer of the transported substance is further attached to a moiety which provides for the selective targeting of the inhibitor to cells which uptake the transported substance.

7. The method of claim 4 wherein said copolymer comprises different polyamines.

8. The method of claim 4 wherein the molecular weight of said polyamine polymer ranges from about 15,000 to 100,000 daltons.

9. The method of claim 4 wherein the treated cells comprise tumor cells or pulmonary artery smooth muscle cells.

10. The method of claim 9 wherein said cells are further contacted with a substance which inhibits the synthesis of polyamines.

11. The method of claim 10 wherein said substance is d-difluoro-methylornithine.

12. The method of claim 9 wherein said cells comprise tumor cells which are further contacted with an anti-tumor agent, and the efficacy of said anti-tumor agent is assessed in relation to control tumor cells which are contacted with said anti-tumor agent but which cells are not contacted with the inhibitor.

13. The method of claim 1 wherein said contacting is effected in vitro in a cell culture medium which contains cells which are capable of uptaking said polyamine or polyamines by active transport.

14. The method of claim 13 wherein said cells are human tumor cells.

15. The method of claim 10 wherein the polyamine synthesis inhibiting substance is a substance which inhibits ornithine decarboxylase.

* * * * *